United States Patent [19]

Kumar et al.

[11] Patent Number: 5,821,367
[45] Date of Patent: Oct. 13, 1998

[54] REGIOSPECIFIC PROCESS FOR SYNTHESIS OF ACYCLIC NUCLEOSIDES

[75] Inventors: Ashoke Kumar; Dharmendra Singh; Mukesh Jagannath Wani; Narendra Sriram Joshi; Pravin Sahadev Thombre; Ajay Singh Rawat, all of Mandideep, Dist. Raisen, M.P., India

[73] Assignee: Lupin Laboratories Limited, Bombay, India

[21] Appl. No.: 628,409

[22] Filed: Apr. 5, 1996

[30] Foreign Application Priority Data

Feb. 22, 1996 [IN] India ................................ 99/BOM/96

[51] Int. Cl.⁶ .................................................. C07D 473/18
[52] U.S. Cl. ................................................. 544/276
[58] Field of Search ............................... 544/276

[56] References Cited

U.S. PATENT DOCUMENTS

| | | | |
|---|---|---|---|
| 4,199,574 | 4/1980 | Schaeffer | 424/200 |
| 4,355,032 | 10/1982 | Verheyden et al. | 424/253 |

FOREIGN PATENT DOCUMENTS

| | | |
|---|---|---|
| 833006 | 3/1976 | Belgium . |
| 0 532 878 | 3/1993 | European Pat. Off. . |
| 59-80685 | 5/1984 | Japan . |
| 63-107982 | 4/1988 | Japan . |
| WO 95/07281 | 3/1995 | WIPO . |

OTHER PUBLICATIONS

Martin, J Med Chem 29, 1384 (1986).
Suzaki, Chem. Pharm. Bull. 18, 172 (1970).

*Primary Examiner*—Mark L. Berch
*Attorney, Agent, or Firm*—Merchant, Gould, Smith, Edell, Welter & Schmidt, P.A.

[57] ABSTRACT

This invention relates to an improved regiospecific process for the synthesis of acyclic nucleosides such as, acyclovir and ganciclovir, anti-viral compounds especially effective against herpes virus, and intermediates thereof starting from dyacylguanine and an alkylating agent, selected from 2-oxa-1,4-butanediol diacetate (OBDDA), 1,4-diacetoxy-3-acetoxymethyl-2-oxa-butane, 1,4-dibenzyloxy-3-acetoxymethyl-2-oxabutane. The reaction is carried out in the absence of an acid catalyst and a solvent.

7 Claims, 5 Drawing Sheets

REGIOSPECIFIC PROCESS FOR SYNTHESIS OF ACYCLIC NUCLEOSIDES

BACKGROUND OF THE INVENTION

1. Field of the Invention

This invention relates to an improved regiospecific process for the synthesis of acyclic nucleosides such as, acyclovir and ganciclovir, anti-viral compounds especially effective against herpes virus, and intermediates thereof starting from diacylguanine and an alkylating agent, selected from 2-oxa-1,4-butanediol diacetate (OBDDA), 1,4-diacetoxy-3-acetoxymethyl-2-oxa-butane, 1,4-dibenzyloxy-3-acetoxymethyl-2-oxabutane.

2. Discussions of the Background

Both acyclovir (Ia) and ganciclovir (Ib) show remarkable anti-viral activities (U.S. Pat. No. 4,199,574, U.S. Pat. No. 4,355,032)

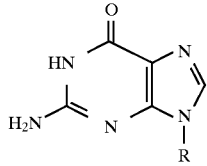

Ia: R=—CH$_2$—O—CH$_2$CH$_2$—OH (Acyclovir)

Ib: R=CH$_2$—O—CH(CH$_2$OH)CH$_2$OH (Ganciclovir)

The strategy adopted in prior art for manufacture of I is alkylation of appropriately substituted 2-aminopurines e.g. guanine derivatives with required addendum which essentially includes an acid with or without solvent to yield N-9 alkylated intermediate (II) e.g. N$^2$-acetyl-9-[(2-acetoxy ethoxy)methyl] guanine (IIa) along with corresponding N-7 alkylated isomer (IIIa). In particular, it is known to react mono or diacetylated guanine with 2-oxa-1,4-butanediol diacetate (OBDDA) to yield the intermediate compound of formula II.

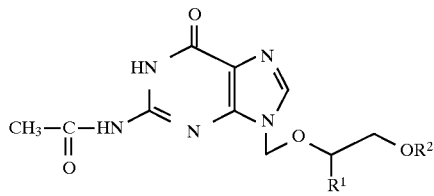

IIa: R$^1$=H, R$^2$=COCH$_3$

IIb: R$^1$=CH$_2$OCH$_2$Ph, R$^2$=CH$_2$Ph

IIc: R$^1$=CH$_2$OCOCH$_3$, R$^2$=COCH$_3$ along with compound of formula III

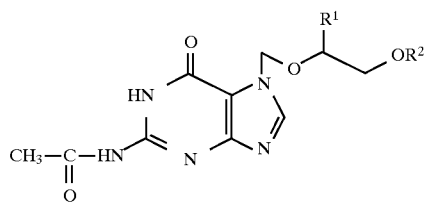

Wherein the formula III includes the compound according to IIIa, IIIb and IIIc, with R$^1$ and R$^2$ as defined in formula IIa, IIb and IIc respectively.

This intermediate mixture of II and III is purified generally by costly and tedious processes to remove the last traces of N-7 isomer (III) and then hydrolysed to yield I. Often N-7 isomer (IV) is associated with final product which is further removed employing a number of operations.

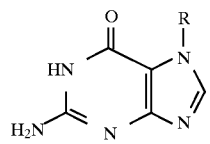

Wherein for IVa and IVb, R is as defined in formula I.

Since alkylation of guanine derivatives like diacetyl/monoacetyl guanine (DAG/MAG) of formula V and VI

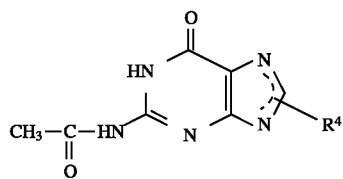

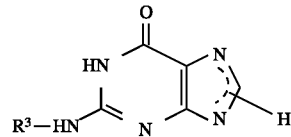

(Va: R$^4$=COCH$_3$, DAG)

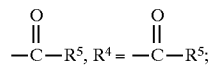

(VIa: R$^3$=COCH$_3$, MAG)
wherein R$^3$=—CHO,
where R$^5$=methyl, ethyl, isopropyl, phenyl;
in presence of an acid, is a thermodynamically controlled reaction, N-7 isomer of formula III is always formed. However, N-9 isomer (II) being thermodynamically more stable (Chem Pharm Bull, 1970, 18, 1446) is produced as the major product.

The formation of N-7 isomer (III) increases the total cost of manufacture. Hence, there is a need for development of regiospecific process for the manufacture of II, the penultimate intermediate for I.

Some of the important methods for manufacture of acyclovir/ganciclovir of formula I reported in the prior art are described below:

1. BE 833 006, U.S. Pat. No. 4,199,547 describe a process for the synthesis of Acyclovir (Ia) which involves condensation of trimethylsilylated guanine with 2-benzoyloxyethyoxy methyl chloride in DMF in the presence of a base followed by deprotection, yielding in the desired N-9 isomer(IIa) along with unacceptable amounts of its corresponding N-7 isomer(IIIa). The former after purification and deacetylation gives acyclovir in 24% overall yield.

2. Matsumoto in Chem Pharm Bull, 36(3), 1153–1157 and JP 63-107982 teaches a process for the synthesis of acyclovir(Ia) by condensation of diacetyl guanine (DAG Va) with 2-oxa-1,4-butanediol diacetate (OBDDA, VIIa) in DMSO in presence of an acid catalyst to get a mixture of N-9/N-7 isomer (66:26). The former is isolated by column chromatography and deacetylated with methanolic ammonia to give acyclovir. Overall yield of acyclovir from guanine is 42%
The process is illustrated in the following scheme A:

SCHEME A

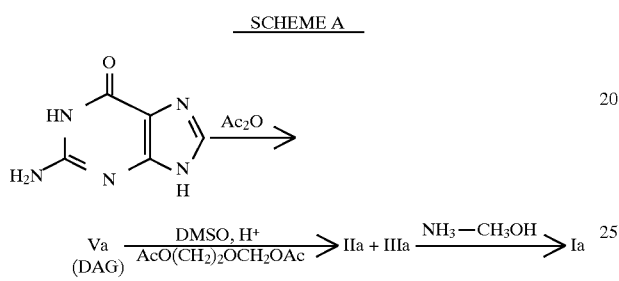

3. JP 59-80685 utilises similar chemistry but starts from $N^2$-monoacetyl guanine (MAG, VIb) in presence or absence of solvent to yield a mixture of N-9 and N-7 alkylated guanine derivatives (N-9/N-7 ratio 52:26). The former subsequently isolated and deprotected to give acyclovir in overall 43% yield.

4. EP 532 878 describes a process in which a transglycosilation reaction between guanosine, acetic anhydride and 2-oxa-1,4-butanediol diacetate (OBDDA) in the presence of catalytic amount of an acid is carried out, followed by hydrolysis to yield a mixture of acyclovir (Ia) and its N-7 isomer (IVa). The above process is illustrated in the following scheme B:

SCHEME B

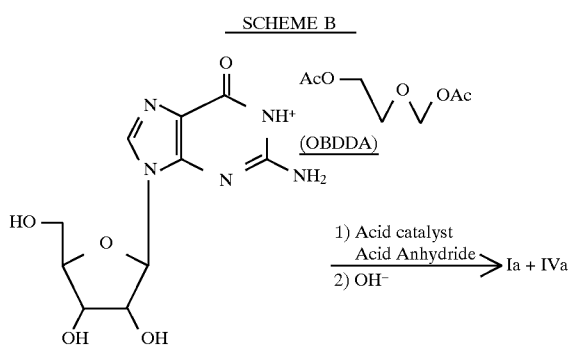

It can be observed that the major drawback in all the processes described above is that acyclovir (Ia) or its Intermediate (IIa) is always contaminated with substantial amount of its N-7 isomer, and hence the separation of the desired N-9 isomer from the mixture is very tedious and requires chromatographic separation or fractional crystallisation.

In addition to the above, the PCT patent specification WO 95/07281 describes a process for the synthesis of Acyclovir (Ia) from $N^2$-formylguanine. The chemistry of the process is illustrated in the following Scheme C:

SCHEME C

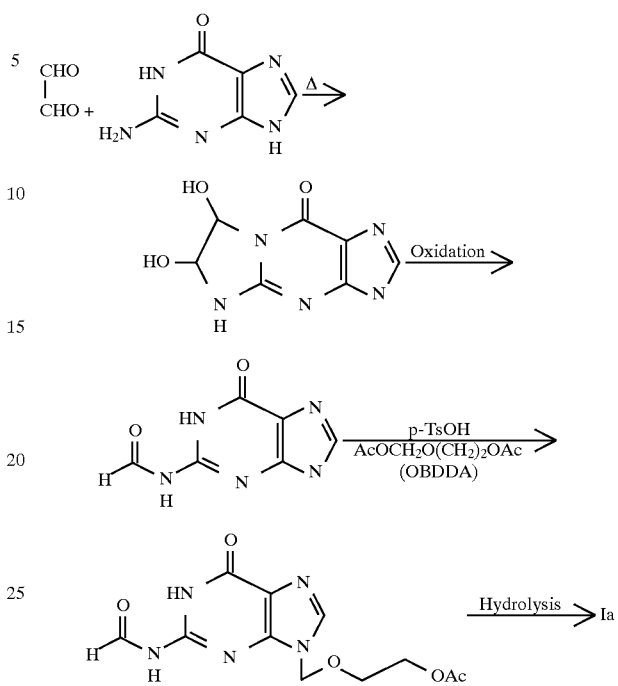

As illustrated in the above scheme, acyclovir is synthesised in four steps:
1) condensation reaction between guanine and glyoxal,
2) oxidation of the resulting tricyclic vicinal diol to $N^2$-formyl guanine
3) alkylation of $N^2$-formylguanine with OBDDA in the presence of an acid,
4) hydrolysis of $N^2$-formyl-$N^9$alkylated guanine to Acyclovir.

The final crude produce is subjected to elaborate purification steps to get guanine free acyclovir of pharmaceutical grade. It is a lengthy process and hence not practical.

It might be highlighted that in the prior art, alkylation of DAG (Va), $N^2$-acetyl guanine(MAG, Via) or $N^2$-formylguanine to the penultimate intermediate of I is always an acid catalysed one; for instance p-toluenesulfonic acid is a common acid although other acids have also been employed [Chem Pharm Bull, 36(3), 1153–1157 (1988)]. Also use of a solvent is preferred in almost all the cases and no attempt has been made for recycle of the undesired N-7 isomer or developing conditions which can lead to selective formation of the desired isomer i.e. II.

Prior art also does not specify the molar ratio of acid catalyst and alkylating agent with respect to protected guanine derivatives for obtaining high N-9/N-7 isomer ratio.

SUMMARY OF THE INVENTION

Accordingly, the basic objective of the present invention is to provide for a simple and cost effective regiospecific process for the synthesis of N-9 alkylated guanine derivatives of general formula II such as $N^2$-acetyl-9-[2-(acetoxyethoxy)methyl]guanine(IIa), $N^2$-acetyl-9-[1,3-bis(benzyloxy-2-propoxy)methyl]guanine(IIb), which would be suitable intermediates for the manufacture of acyclic nucleosides of formula I such as acyclovir and ganciclovir having desired characteristics for its therapeutic use as anti-viral agents.

A further object of the invention is to provide a process for the recycle of the N-7 isomer of formula III to its thermodynamically more stable N-9 isomer of formula II.

Other objects will be apparent from the description of the invention given herein below.

In accordance with the above basic objectives of the present invention in an aspect of the invention there is provided a regiospecific process for the manufacture of intermediate compound of formula I for use in synthesis of acyclic nucleocides of formula I which comprises reacting a substituted guanine derivative of formula V,

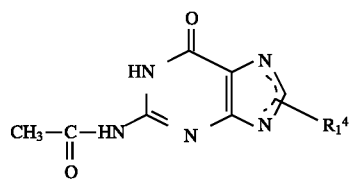

wherein

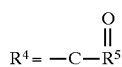

where $R^5$=methyl, ethyl, isopropyl, phenyl with alkylating agent of formula VII,
wherein $R^1$ and $R^2$ is as defined in formula II, without the presence of any acid catalyst and/or solvent under modified conditions comprising carrying out said reaction between protected guanine derivative and said alkalyting agent in the molar ratio of 1.5 to 6.0 preferably 1.5 to 2.5 at a temperature ranging from 90°–170° preferably between 100° C.–110° C. for a period of 75–80 hrs.

Such an aspect of the invention is schematically represented as follows:

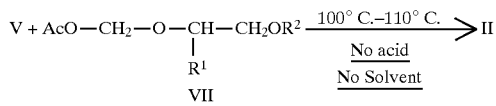

Wherein formula VII is representative of formuli VIIa, VIIb and VIIc, with $R^1$ and $R^2$ as defined in formula IIa, IIb and IIc respectively.

Another aspect of the invention there is provided a process for producing practically pure acyclic nucleocides of formula I such as acyclovir and ganciclovir from the compound of formula II obtained as above by basic hydrolysis. Such an aspect of the invention is represented by the following steps:

i) washing the crude intermediate (II) with a solvent selected from methanol, ethanol, iso-propanol, acetone, THF, dioxane, dimethoxyethane, acetonitrile, toluene, benzene, ethyl acetate, dichloromethane or mixture thereof to remove the traces of non-polar impurities.

ii) deprotection of the various functional groups such as esters, or benzyl ethers of the intermediate (II) to yield pure N-9 isomer (I) i.e acyclovir or ganciclovir of extremely high purity.

Another aspect of the invention provides for a simple method of recycling N-7 isomer of formula III to its more thermodynamically stable N-9 isomer of formula II by heating said N-7 isomer in the presence of OBDDA without any acid or solvent in the temperature range of 100°–110° C. for a period of 10–20 hours preferably 13–15 hours to thereby produce a mix of N-9 and N-7 isomer the former constituting the major portion of said mix.

Other aspects of the invention will become apparent from the description of the present invention given herein below.

DETAILED DESCRIPTION OF THE INVENTION

With the objectives of the present invention discussed above in mind, extensive study on the subject made by the present inventors revealed that in the presence of an acid catalyst and a solvent, the alkylation reaction of DAG(Va) and OBDDA, gives significant proportion of N-7 isomer (III) along with other side products and also poor yields of N-9 isomer (II). Thus, in a homogeneous mixture of DAG (Va), OBDDA, p-toluene sulfonic acid (p-TsOH) and a solvent, the ratio of N-9 to N-7 isomer varies from 2.3 to 2.6. Further, with higher concentration of acid the ratio of N-9/N-7 isomer is observed to come down substantially as is clearly illustrated in Table 1 hereunder.

TABLE 1

Effect of various concentrations of p-TsOH on N-9/N-7 ratio (of II & III)

Reactants:
Diacetyl guanine (Va): 10 gms (0.0425 moles)
OBDDA (VIIa): 18.7 gms (0.106 moles)
Reaction Conditions: Reaction mixture heated at 100° C.–105° C. in a round bottom flask.

| | Amt of p-TsOH.H$_2$O used | | | HPLC monitoring of condensation reaction | | | |
|---|---|---|---|---|---|---|---|
| | | | | | | % ratio calculated | |
| Sr No | Gms | moles × 10$^{-3}$ | molar ratio pTsOH/ DAG | Reaction Time Hr | N-9 isomer | N-7 isomer | N-9 isomer | N-7 isomer |

| Sr No | Gms | moles × 10$^{-3}$ | pTsOH/DAG | Time Hr | N-9 | N-7 | N-9 | N-7 |
|---|---|---|---|---|---|---|---|---|
| 1 | 0 | 0 | 0 | 70 | 95.60 | 2.90 | 97.05 | 2.94 |
| 2 | 0.05 | 0.265 | 0.0063 | 28 | 92.60 | 3.70 | 96.45 | 3.54 |
| 3 | 0.10 | 0.53 | 0.0125 | 21 | 90.10 | 5.10 | 94.64 | 5.36 |
| 4 | 0.19 | 1.06 | 0.0250 | 15 | 82.90 | 5.70 | 93.56 | 6.43 |
| 5 | 0.40 | 2.12 | 0.050 | 15 | 80.20 | 6.50 | 92.50 | 7.50 |
| 6 | 0.80 | 4.21 | 0.100 | 15 | 77.50 | 7.90 | 90.70 | 9.20 |

Figure 1:
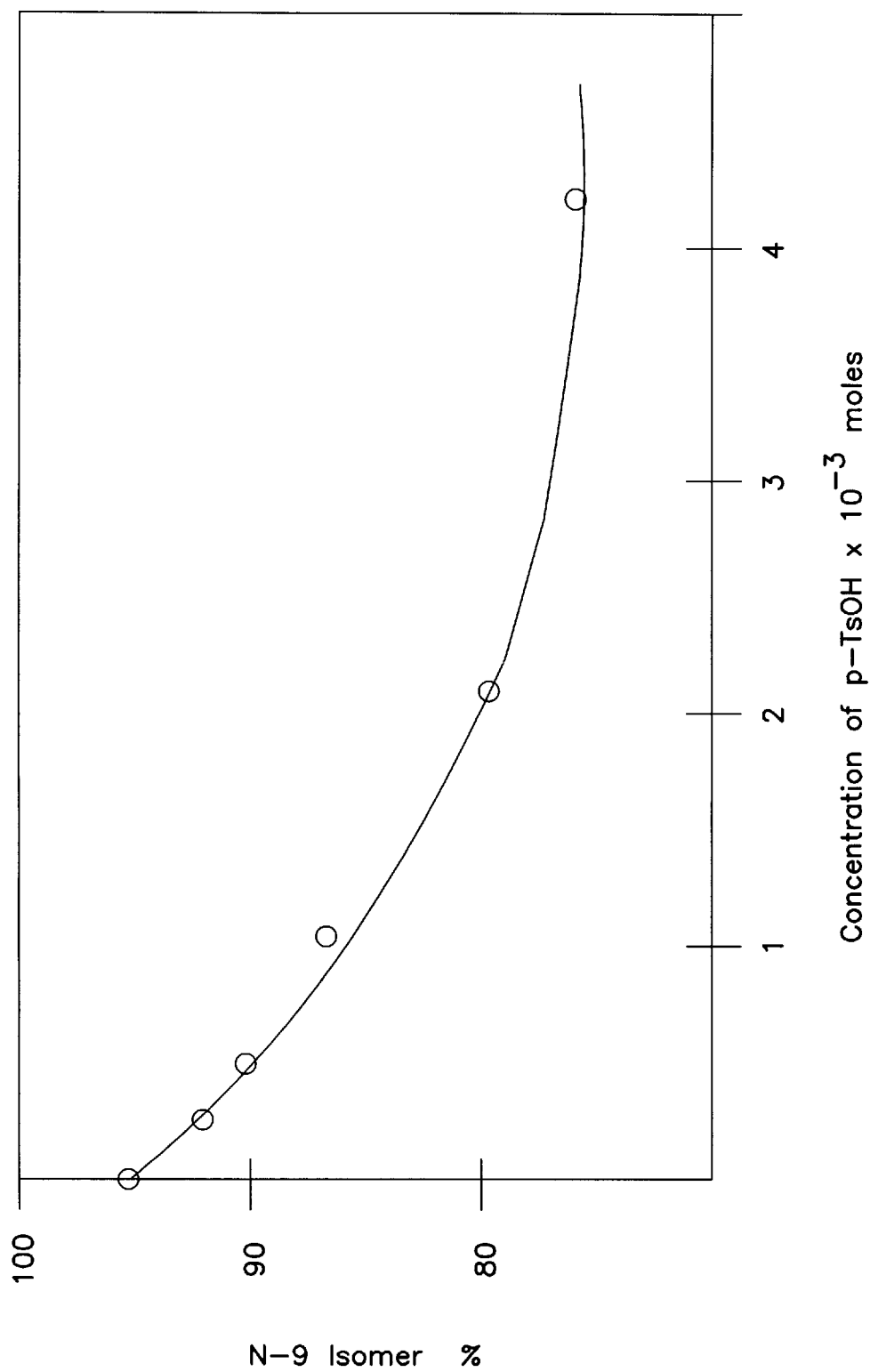
FIG. 1 is a graph illustrating the relationship between percentage of N-9 isomer and concentration of p-TsOH.

From Table 1, one would observe that with higher concentration of acid, the ratio of N-9/N-7 isomer comes down substantially. The same data is plotted in FIG. 1.

The inventors further observed that N$^2$-acetylguanine i.e. N$^2$-monoacetylguanine(MAG, VIa) cannot be alkylated in the absence of acid catalyst by OBDDA. However, surprisingly enough the inventors have identified that the compound of formula V such as diacetylguanine (DAG, Va) can be converted to the intermediate (II) in the presence of OBDDA or the corresponding alkylating agents used to synthesis ganciclovir without the aid of any acid catalyst or solvent only when reacted under specific modified reaction conditions.

Figure 2:
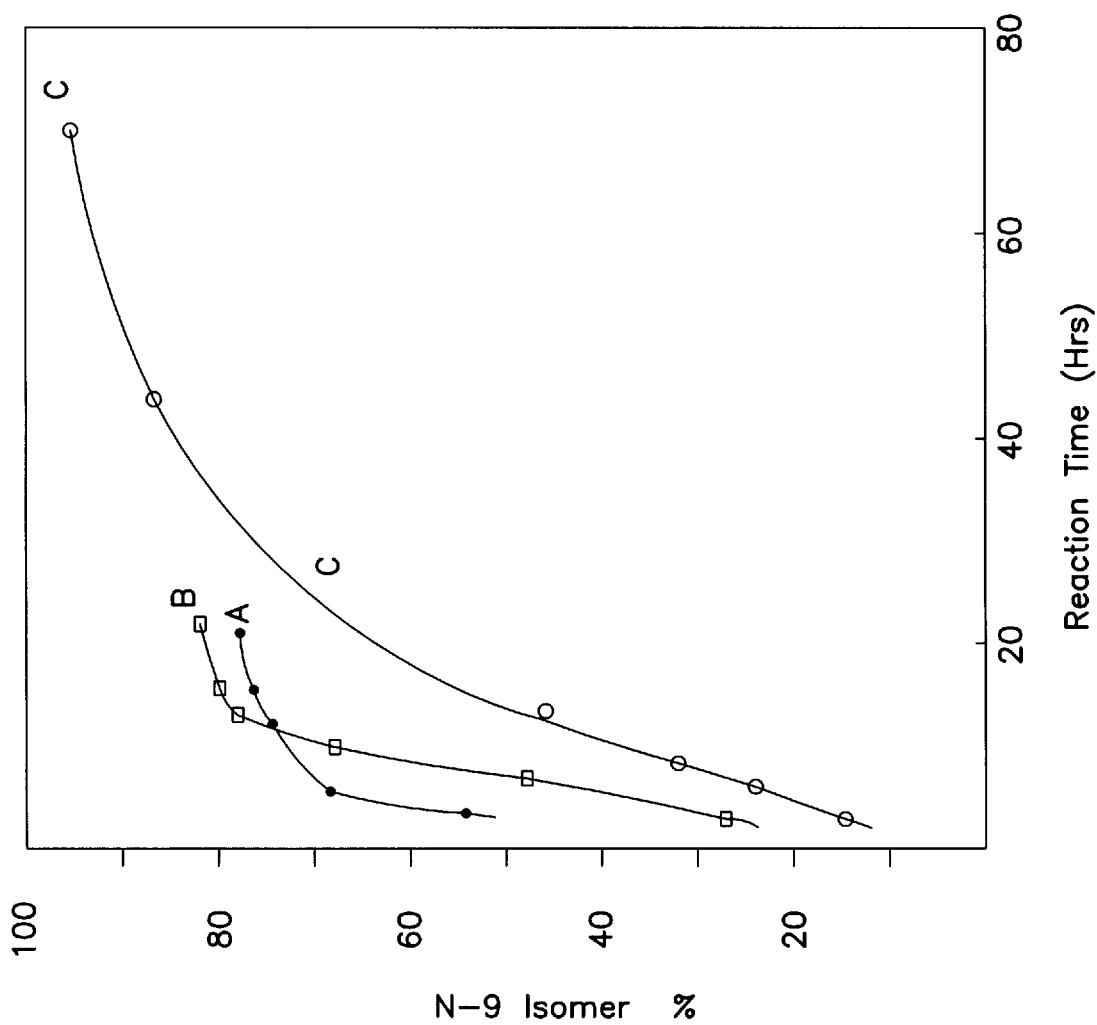
FIG. 2 is a graph illustrating the relationship between percentage of N-9 isomer and reaction time for three different concentrations of p-TsOH.

Thus, the present inventors have found that under said specific modified reaction conditions and in the absence of any acid catalyst and solvent although the reaction between DAG (Va) and OBDDA was slower but such conditions provided much purer N-9 isomer (IIa) with very little concomitant formation of the undesired N-7 isomer. Such findings of the invention are illustrated hereunder in Table 2 which indicates the rate of formation of N-9 isomer of formula IIa using two different concentrations of the acid catalyst viz. p-toluene sulphonic acid and without any such acid. The formation of N-9 isomer was monitered through HPLC analysis and the results are further plotted in FIG. 2.

TABLE 2

Comparison of rate of formation of N-9 isomer in the presence and absence of p-toluene sulfonic acid.$H_2O$ (p-TsOH.$H_2O$).
Reactants:
Diacetyl guanine (Va): - 10 gms (0.0425 moles)
OBDDA (VIIa):          - 18.7 gms (0.106 moles)
Reaction Conditions:   Reaction mixture heated at 100°C.–105° C.,

| P-TsOH.$H_2O$ moles × $10^{-3}$ | A | B | C |
|---|---|---|---|
| Sr No. | Reaction Times Hrs | 4.21 | 1.06 | 0 |
| | | % N-9 Isomer formed* | | |
| 1 | 03 | 55.20 | 28.50 | 15.1 |
| 2 | 06 | 69.10 | 49.20 | 24.6 |
| 3 | 09 | 70.20 | 69.10 | 31.9 |
| 4 | 12 | 73.10 | 77.20 | 44.16 |
| 5 | 15 | 76.30 | 80.50 | 85.3 (44 hrs) |
| 6 | 21 | 77.50 | 81.20 | 95.6 (70 hrs) |

*Based on HPLC monitoring of the alkylation step.

The above table 2 clearly reveals that the formation of N-9 isomer is more when the alkylation reaction is carried out in the absence of any acid as compared to the use of the acid when the reaction time is allowed to proceed beyond 15 hrs.

Figure 3:
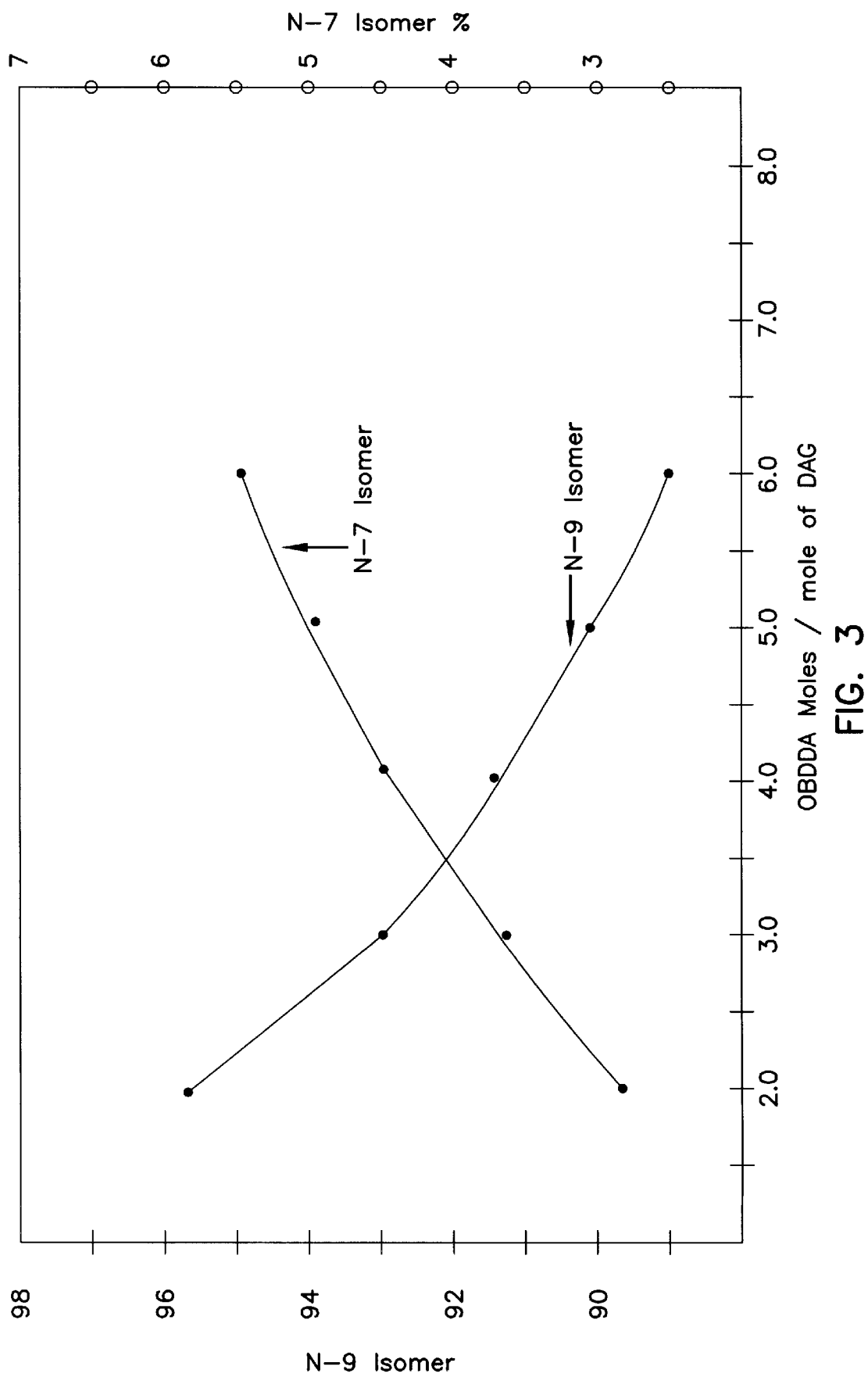
FIG. 3 is a graph illustrating the relationship between the percentages of N-7 and N-9 isomer and the relative amounts of OBDDA and DAG.

With such findings of favourable yield of N-9 isomer in the absence of any acid catalyst for the alkylating reaction of diacetyl guanine with OBDDA, the dependants of molar proportion of the two reactants on the yield of N-9 isomer of formula II in the absence of acid was determined. The results are reproduced hereunder under Table 3 and further represented in FIG. 3.

TABLE 3

Effect of concentration of OBDDA on N-9/N-7 isomer formation without acid catalyst
Reaction temperature: 100° C.–105° C.

| Sr No | OBDDA Used moles/mole DAG | % N-9 isomer* IIa | % N-7 isomer* IIIa | Reaction time Hrs |
|---|---|---|---|---|
| 1 | 2.0 | 95.6 | 2.9 | 75 |
| 2 | 3.0 | 93.0 | 3.6 | 60 |
| 3 | 4.0 | 91.5 | 4.5 | 46 |
| 4 | 5.0 | 90.6 | 4.7 | 38 |
| 5 | 6.0 | 89.0 | 5.4 | 33 |

*determined by HPLC monitoring of the reaction.

As evident from table 3 above, though with higher proportion of OBDDA the rate of reaction is faster, however yields tend to be lower and the best yield is obtained when approximately two moles of OBDDA per mole of DAG(Va) is used. Thus, when the molar ratio between OBDDA and DAG is 2 and no acid or no solvent is used and the mixture is heated at 100° C.–110° C. for 75–80 hour, a mixture of >95% of N-9 isomer of IIa and <3% of the corresponding N-7 isomer is obtained.

The observation that the alkylation of DAG(Va) with OBDDA, 1,4-diacetoxy-3-acetoxymethyl-2-oxa-butane or similar alkylating agents, is also a thermodynamically controlled reaction even in the absence of an acid catalyst and a solvent is novel.

Thus the above teachings further indicated that either N-9 isomer(II) or its corresponding N-7 isomer (III) could be equilibrated to a mixture of both the isomers even in the absence of acid and solvent.

The invention accordingly thus further identifies that when the aforesaid N-9 isomer or N-7 isomer is heated at 100° C.–110° C. in the presence of OBDDA and in the absence of an acid and solvent, a mixture of N-9 and N-7 isomers is indeed obtained, the former being the major product.

Figure 4A:
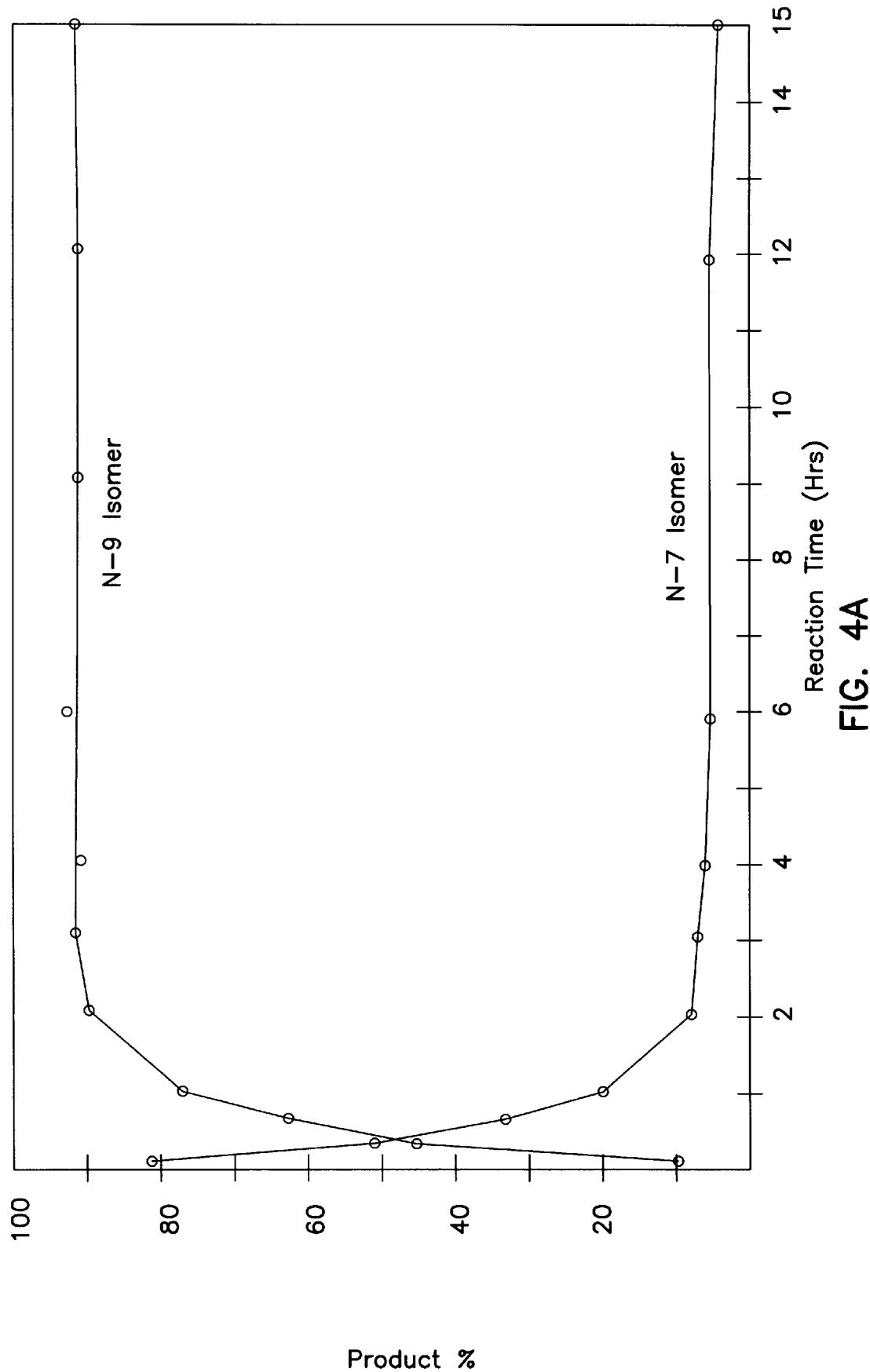
FIGS. 4A and 4B illustrate the relationship between percentage of N-7 and N-9 isomer and the reaction time.
Figure 4B:
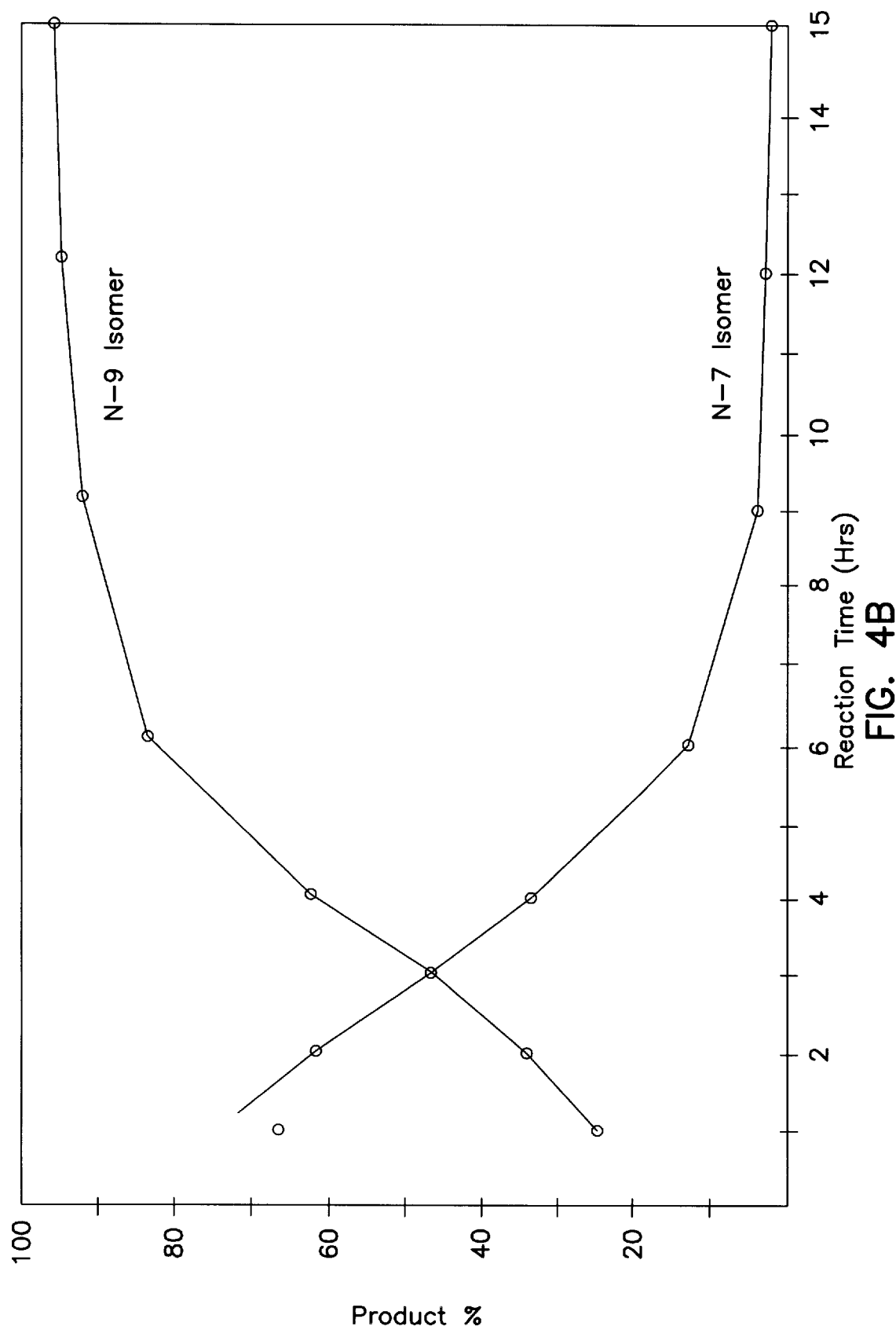

The rate of isomerisation of N-7 isomer to N-9 isomer in the presence and absence of an acid was studied and the details are represented hereunder in Table 4 which is further illustrated in FIG. 4a and 4b.

TABLE 4

Equilibrium study of N-7 isomer (IIIa) at 100° C.–104° C.

| Sr No | Reaction Time Hrs | With p-TsOH | | Without P-TsOH | |
|---|---|---|---|---|---|
| | | % N-9 | % N-7 | % N-9 | % N-7 |
| 1 | 00.083 | 09.57 | 81.13 | — | — |
| 2 | 00.330 | 45.00 | 50.40 | — | — |
| 3 | 00.660 | 62.43 | 32.88 | — | — |
| 4 | 01.000 | 76.90 | 19.58 | 24.67 | 66.55 |
| 5 | 02.000 | 89.50 | 07.62 | 33.93 | 61.76 |
| 6 | 03.000 | 91.30 | 06.88 | 46.84 | 46.49 |
| 7 | 04.000 | 90.63 | 05.90 | 62.38 | 33.37 |
| 8 | 06.000 | 92.60 | 05.43 | 83.40 | 12.98 |
| 9 | 09.000 | 91.00 | 05.54 | 91.84 | 03.89 |
| 10 | 12.000 | 90.84 | 05.36 | 94.50 | 03.33 |
| 11 | 15.000 | 91.44 | 04.49 | 95.70 | 02.72 |

The above results in table 4 therefore clearly illustrate that in the presence of an acid catalyst N-7 isomer isomerises to 91.44% of N-9 isomer with 4.5% of N-7 isomer remaining, whereas in the absence of acid under identical conditions the isomerisation takes place to the extent of 95% of N-9 isomer in 15 hours. The isomerisation of pure N-9 isomer(IIa) when studied under identical conditions, was found to give almost similar ratios of N-9 and N-7 isomers in acid catalysed and non-catalysed reactions as reported (see table IV) for N-7 isomer.

The effect of temperature on the rate of reaction on the ratio of isomer distribution and the yield is quite significant. It has been observed that the yield of N-7 isomer is more at higher temperatures than that at lower temperatures.

Moreover, an acid catalysed reaction at higher temperatures gives lower yields than that of the reaction without any acid catalyst. Higher temperature tends to produce more impurities/side products.

Thus by way of the above the present invention provides that under modified conditions comprising fusion reaction between protected guanine derivatives of structure (V) and alkylating agent (VII) in the molar ratio of 1.5 to 6 at a temperature ranging from 90°–170° C., preferably between 100° C.–110° C., in absence of solvent of catalyst for 75–80 hours it is possible to obtain the compound of formula II and also synthesis of acyclic nucleosides from such compounds of formula II by way of a simple and cost effective process of manufacture.

The objects, advantageous and means of attaining the same as also the scope of the present invention will hereinafter be illustrated in greater detail by way of the following non-limiting examples. It should be understood that the invention is not intended to be limited to the specific examples.

EXAMPLES

Example 1
$N^2$, $N^9$ Diacetyl guanine(DAG, Va):

A mechanically stirred heterogeneous mixture of guanine (22.65 g, 0.15 mole), acetic anhydride (91.8 g, 0.9 mole) and p-toluene sulphonic acid monohydrate (0.70 g, 3.75×10$^{-3}$ mole) is heated at 130° C.–135° C. for 12–14 hours. After the completion of the reaction (monitored by HPLC), the reaction mixture is cooled to room temperature and filtered using cintered funnel. The solid thus obtained is washed with toluene (3×25 ml) and dried at 70° C.–80° C. under vacuum for 4–5 hours to give 33.1 g (93.9%) diacetyl guanine (DAG), m.p. 300° C.(dec)

PMR(DMSO-d$_6$)δppm: 8.5(s, 1H, H), 2.85 (s,3H, $N^9$—COCH$_3$),2.2(s,3H, $N^2$—COCH$_3$)

IR(KBr)cm$^{-1}$: 3150, 1720, 1705, 1685, 1605, 1528, 1220, 619.

HPLC Conditions: Column C$_{18}$ (reverse phase); eluent, CH$_3$CN: water; 20:80 adjusted to pH2; detector, UV 254 nm, flow rate 2 ml per minute.

Example 2
$N^2$-Acetyl-9-[(2-acetoxyethoxy)methyl] guanine (N-9 isomer, IIa) with acid catalyst.

A stirred mixture of DAG (10 g, 0.0425 mole), OBDDA (18.7 g; 0.106 mole) and p-TsOH.H$_2$O (0.19 g, 0.001 mole) was heated in a round bottom flask at 105° C.–110° C. for 15 hours. The reaction mixture was concentrated under vacuum and the residue was column chromatographed on SiO$_2$ column using CH$_2$Cl$_2$—CH$_3$OH (60:40 v/v) solvent system to give the desired N-9 isomer in 85–86% isolated yields, m.p. 189° C.–190° C.

PMR(DMSO-d$_6$(δ ppm: 12.1 (bs, 1H, HNCOCH$_3$) 11.85 (bs, 1H, NH), 8.2 (s, 1H, H), 5.5 (s, 2H, NCH$_2$O), 4.15 (m, 2H, OCH$_2$), 3.7 (m, 2H, OCH$_2$), 2.2 (s, 3H, NCOCH$_3$), 1.95 (s, 3H, NCOCH$_3$).

Example 3
$N^2$-Acetyl-9-[(2-acetoxyethoxy)methyl] guanine (N-9 isomer IIa) without acid catalyst Diacetylguanine (DAG) (10 g, 0.0425 mole) and OBDDA (18.7 g, 0.106 mole) is heated in a round bottom flask at 105° C.–110° C. under continuous stirring for 75–80 hours. After almost complete conversion of DAG, the excess of OBDDA was distilled out and the residue was heated with a mixture of toluene:methanol (25:75, 25 ml) at 45°–50° C. for 30 minutes and the solid was collected by filtration at 5° C.–10° C. to yield 98.8% pure (by HPLC) N-9 isomer in 91.0% isolated yield.

Example 4
$N^2$-Acetyl-9-[(2-acetoxyethoxy)methyl] guanine (N-9 isomer, IIa):

A stirred mixture of DAG (10 g, 0.042 mole) and OBDDA (18.7 g; 0.106 mole) was heated in a round bottom flask at 105° C.–110° C. for 80 hours. The reaction mixture was concentrated under vacuum and the residue was column chromatographed on SiO$_2$ column using CH$_2$Cl$_2$:MeOH (6:4 v/v) to give the desired N-9 isomer in ≧94% isolated yields, m.p. 189° C.–190° C.

Example 5
$N^2$-Acetyl-9-[(2-acetoxyethoxy)methyl] guanine (N-9 isomer, IIa):

A stirred mixture of DAG (10 g, 0.0425 mole), OBDDA (44.9 g; 0.255 mole) and p-TsOH.H$_2$O (0.19 g, 0.001 mole) was heated in a round bottom flask at 100° C.–105° C. for 20 hours. Excess OBDDA was removed under vacuum and the residue thus obtained was diluted with toluene (50 ml) and heated at 100° C. for 2 hours. The reaction mixture is then cooled at 50° C. and filtered to get 11.30 g (87%) crude product.

Purification of crude product

A suspension of the above obtained crude N-9 isomer (11.30 g) in toluene:isopropyl alcohol (1:1, 50 ml) was heated in round bottom flask at 75° C.–80° C. for 2 hours. The reaction mixture is then cooled to 0° C.–5° C., maintained at the same temperature for 1 hour and filtered to get 10.6 g (80%) N-9 isomer of more than 99% HPLC purity.

Example 6
$N^2$-Acetyl-7-[(2-acetoxyethoxy)methyl] guanine (N-7 isomer):

A mixture of DAG (23.5 g, 0.1 mole), OBDDA (61.6 g; 0.35 mole) and p-TsOH.H$_2$O (0.475 g, 2.5×10$^{-3}$ mole) in acetic acid (75 ml) was heated in a round bottom flask at about 110° C. under continuous stirring for 8 hours. The temperature of the reaction mixture was brought down to 50° C. and acetic acid was removed by distillation under vacuum. The residue obtained after removing acetic acid was extracted with benzene (3×50 ml) and the combined extract was concentrated under vacuum to give a thick oily residue which was purified by passing through a column of SiO$_2$ using CH$_2$Cl$_2$—CH$_3$OH(80:20 v/v) solvent system to yield N-7 isomer (10 g) of 87% HPLC purity.

PMR (DMSO-d$_6$) ppm: 12.5 (bs, 1H, CONH); 11.6 (bs, 1H, CONH); 8.2 (s, 1H, H), 5.5 (s, 2H N—CH$_2$—O); 4.1 (m, 2H, OCH$_2$O); 3.70 (m, 2H, OCH$_2$); 2.2 (s, 3H, OCOCH$_3$) 1.95 (s, 3H, NCOCH$_3$).

Example 7
Isomerisation of N-7 isomer to N-9 isomer in presence of p-TsOH

A heterogeneous mixture of N-7 isomer (0.4 g, 0.013 mole; 87% pure) and OBDDA (1.14 g, 0.065 mole) in presence of p-TsOH.H$_2$O (0.062 g, 0.325×10$^{-3}$ mole) was heated at 100° C.–110° C. under continuous stirring and the progress of the reaction was monitored by HPLC. Samples were withdrawn at regular time intervals and analysed by HPLC. The data is presented in Table IV.

Example 8
Isomerisation of N-7 to N-9 in absence of p-TsOH

The isomerisation of the N-7 isomer in absence of P-TsOH was performed under identical conditions as given in the above experiment (e.g. 7). Samples were withdrawn at regular time intervals and analysed by HPLC techniques. The data is presented in Table IV. The transformation of N-7 to N-9 isomer as monitored by HPLC was found to be comparatively very slow and took almost 15 hours to reach equilibrium (for details see Table-IV, FIG. 4b).

Example 9
$N^2$-acetyl-9[(2-acetoxyethoxy)methyl] guanine: Effect of concentration of acid catalyst on the rate of the reaction A suspension of DAG (10 g, 0.0425 moles) in OBDDA (18.7 g, 0.106 moles) was heated in the presence of different amounts of TsOH.H$_2$O and also in the absence of the latter at 100° C.–105° C. Samples were withdrawn at regular time intervals and analysed by HPLC. The data is presented in Table II.

Example 10
9-[(2-Hydroxyethoxy)methyl] guanine (Acyclovir):

To a solution of NaOH pellets (3.8 g, 0.097 mole) in water (100 ml) is added N-9 isomer (10 g, 0.323 mole) at room temperature. The reaction mixture is heated at 85° C.–95° C. for 3 hours. After bringing the temperature down to room temperature the pH of the clear solution is adjusted to pH 7 using 35% HCl and filtered to yield ≧95% of the product of very high quality, m.p. 253° C.

PMR(DMSO-d$_6$)δ ppm: 10.7 (s, 1H, NH), 7.85 (s,1H, H), 6.51 (s, 2H, N—CH$_2$—O) 5.3 (s, 2H, NH$_2$); 4.70 (m, 1H, OH), 3.45 (m, 2H, OCH$_2$), 3.3 (m, 2H, OCH$_2$).

Example 11
N$^2$-Acetyl-9-[(1,3-bis(benzyloxy)-2-propxy) methyl] guanine (N-9 isomer; II$_b$):

A mixture of DAG (5 g, 0.021 mole), 2-O-(acetoxymethyl)-1,3-di-O-benzylglycerol (10.9 g, 0.032 mole) was heated in a round bottom flask under stirring at 110° C.–115° C. for 75–80 hours. The reaction mixture was cooled to room temperature and extracted with hexane (3×15 ml). The residue thus obtained was column chromatographed on SiO$_2$ column using ethylacetate:hexane (50:50 v/v) solvent system to give the desired N-9 isomer (m.p 147° C.) in 68.7% yield. The yield of the N-7 isomer (m.p 133° C.–134° C.) obtained from column was found to be 14.86%.

PMR (DMSO-d$_6$ ppm (N-9 isomer): 8.13 (s, H, H-8), 7.35 (m, 10H, ArH), 5.59 (s, 2H, H-1'); 4.41 (s, 4H, benzylic), 4.05 (m, 1H, H-4'), 3.41 (m, 4H, H-3' & H-5'); 2.18(s, 3H, CH$_3$)

PMR (DMSO d$_6$) ppm (N-7 isomer): 8.34 (s, H, H-8), 7.35 (m, 10H, ArH), 5.80 (s, 2H, H-1'); 4.42 (s, 4H, benzylic), 4.14 (m, 1H, H-4'), 3.48 (m, 4H, H-3' & H-5'); 2.19(s, 3H, CH$_3$)

Example 12
9-[(1,3-dihydroxy-2-propoxy)methyl]guanine (ganciclovir):

The synthesis of Ganciclovir starting from N$^2$-acetyl-9 [1,3-bis (benzyloxy)-2-propoxy) methyl] guanine (N-9 isomer, II$_b$) obtained from example. No. 11 was carried out following the reported conditions (J C Martin et al J. Med. Chem. 1983, 26, 759–761) to get the desired product of high purity in 76% isolated yield, m.p.>300° C.

PMR (DMSO-d$_6$)δ: 10.64(bs, 1H, NH), 7.81(s 1H, H-8), 6.5 (s, 2H, NH$_2$), 5.44(s, 2H, H-1'), 4.63 (p, J=6 Hz, 1H, H-4'), 3.35 (m, H-3' & H-5')

We claim:

1. A regiospecific process for the synthesis of compounds of formula II,

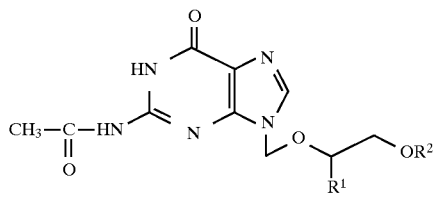

wherein

IIa: R$^1$=H, R$^2$=COCH$_3$
IIb: R$^1$=CH$_2$OCH$_2$Ph, R$^2$=CH$_2$Ph
IIc: R$^1$=CH$_2$OCOCH$_3$, R$^2$=COCH$_3$ which comprises reacting a substituted guanine derivative of formula V,

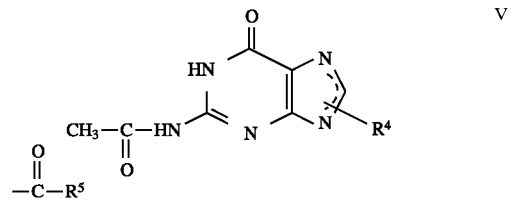

wherein

where R$^5$=methyl, ethyl, isopropyl, phenyl with alkylating agent of formula VII,

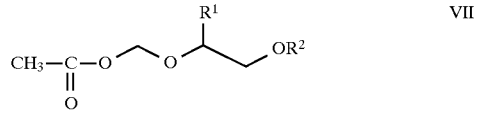

wherein R$^1$ and R$^2$ are as defined in formula II, without the presence of any acid catalyst and/or solvent under modified conditions comprising carrying out said reaction between the substituted guanine derivative and said alkalyting agent in the molar ratio of 1.5 to 6.0 at a temperature ranging from 90°–170° for a period of 75–80 hrs.

2. A process as claimed in claim 1 wherein the compound of formula II is N$^2$-acetyl-9-[(2-acetoxyethoxy)methyl] guanine (IIa) obtained by reacting diacetylguanine (DAG) of formula V with 2-oxa-1,4-butandiol diacetate (OBDDA) of formula VII.

3. A process as claimed in claim 1 wherein the compound of formula II is N$^2$-acetyl-9-[1,3-bis(benzyloxy)-2-propoxy) methyl]guanine(IIb) obtained by reacting diacetyl-guanine (DAG, Va) with 1,4-dibenzyloxy-3-acetoxymethyl-2-oxabutane of formula VII.

4. A process of claim 1 wherein the compound of formula II is purified by washing with solvents selected from methanol, ethanol, iso-propanol, dioxane, THF, 1,2-dimethyoxyethane, acetonitrile, toluene, benzene, dichloromethane, ethyl acetate or mixture thereof.

5. A process as claimed in claim 1, wherein the molar ratio is from 1.5 to 2.5.

6. A process as claimed in claim 1, wherein the temperature range is from 100° C.–110° C.

7. A process as claimed in claim 5, wherein the temperature range is from 100° C.–110° C.

* * * * *